(12) United States Patent
Putnam

(10) Patent No.: US 7,968,062 B1
(45) Date of Patent: Jun. 28, 2011

(54) DRUG DISPOSAL AND VERIFICATION DEVICE

(76) Inventor: Richard Carle Putnam, Searcy, AR (US)

( * ) Notice: Subject to any disclaimer, the term of this patent is extended or adjusted under 35 U.S.C. 154(b) by 397 days.

(21) Appl. No.: 12/217,335

(22) Filed: Jul. 3, 2008

Related U.S. Application Data

(60) Provisional application No. 60/958,646, filed on Jul. 6, 2007.

(51) Int. Cl.
| | |
|---|---|
| G01N 15/06 | (2006.01) |
| G01N 33/00 | (2006.01) |
| G01N 33/48 | (2006.01) |
| G01N 21/75 | (2006.01) |
| G01N 31/22 | (2006.01) |
| G01N 33/52 | (2006.01) |
| B01L 3/00 | (2006.01) |
| B01L 99/00 | (2006.01) |
| G01N 21/03 | (2006.01) |

(52) U.S. Cl. ....... 422/559; 422/68.1; 422/401; 422/430; 422/500; 422/547; 436/165

(58) Field of Classification Search .................. None
See application file for complete search history.

(56) References Cited

U.S. PATENT DOCUMENTS

| | | | |
|---|---|---|---|
| 2,533,089 A | 12/1950 | Brewer et al. | |
| 2,874,091 A | 7/1956 | Fisk | |
| 3,036,894 A | 5/1962 | Forestiere | |
| 3,055,808 A | 9/1962 | Henderson | |
| 3,912,596 A | 10/1975 | Haque | |
| 3,985,264 A | 10/1976 | Shaw et al. | |
| 4,042,463 A | 8/1977 | Haque | |
| 4,690,801 A | 9/1987 | Anderson | |
| 4,707,450 A | 11/1987 | Nason | |
| 4,752,448 A | 6/1988 | Wells et al. | |
| 4,769,333 A | 9/1988 | Dole et al. | |
| 4,801,548 A | 1/1989 | Takakura et al. | |
| 4,943,522 A * | 7/1990 | Eisinger et al. | 435/7.25 |
| 4,992,296 A | 2/1991 | Gibson | |
| 5,119,830 A | 6/1992 | Davis | |
| 5,141,875 A | 8/1992 | Kelton et al. | |
| 5,229,297 A | 7/1993 | Schnipelsky et al. | |
| 5,275,043 A * | 1/1994 | Cotton | 73/261 |
| 5,457,054 A | 10/1995 | Geisinger et al. | |
| 5,496,520 A | 3/1996 | Kelton et al. | |
| 5,611,782 A | 3/1997 | Haedt | |
| 6,043,097 A * | 3/2000 | Dumitrescu et al. | 436/48 |
| 6,108,588 A | 8/2000 | McGrady | |
| 6,576,193 B1 * | 6/2003 | Cui et al. | 422/58 |
| 6,669,908 B2 | 12/2003 | Weyker et al. | |
| 7,384,599 B2 | 6/2008 | Brewer et al. | |
| 2003/0027359 A1 * | 2/2003 | Hudak et al. | 436/518 |
| 2004/0151624 A1 | 8/2004 | Brewer et al. | |

* cited by examiner

*Primary Examiner* — Jill Warden
*Assistant Examiner* — Charles Hammond
(74) *Attorney, Agent, or Firm* — Robert O. Blinn

(57) ABSTRACT

A drug disposal and verification device includes a first chamber and a second chamber. The first chamber has an injection port for receiving wasted drug solution and a disposal volume. A positive displacement flow measuring device positioned between the injection port and the disposal volume is used to measure the volume of wasted drug solution injected into the device. The positive displacement flow measuring device is also adapted to divert a small portion of the wasted drug solution to the second chamber. The second chamber holds a breakable test reagent ampule for quantitative testing of the wasted drug solution. The disposal volume of the first chamber may include at least one test strip for qualitative testing of the wasted drug solution.

9 Claims, 7 Drawing Sheets

DRUG DISPOSAL AND VERIFICATION DEVICE

CROSS REFERENCES TO RELATED APPLICATIONS

This application claims the benefit of U.S. Provisional Patent Application. No. 60/958,646 filed Jul. 6, 2007, which is incorporated herein by witness.

FIELD OF THE INVENTION

This invention relates to a device for receiving an injectable narcotic solution for disposal, measuring the quantity of solution wasted and for verifying the contents of the wasted solution.

BACKGROUND OF THE INVENTION

This invention relates to the disposal and positive verification of the disposal of drugs, and more particularly to the verified disposal of drugs which may be controlled substances, such as, for example, narcotics. Hospitals and medical offices may handle narcotics and other controlled substances. In many cases, a quantity of excess injectable drug remains after the drug has been administered to a patient. Such excess injectables are typically "wasted" preferably in a supervised manner so that the disposal of the drug is witnessed.

Medical professionals and health care workers may come in contact with narcotic agents intended for disposal. Accordingly, medical professionals and health care worker may be tempted to divert a drug for his or her own use or for the monetary rewards that may be gained from diverting a narcotic rather than disposing of the excess drug. Moreover, medical professionals and health care workers would benefit from a means which would verify the proper disposal of excess drugs. Accordingly, a need exists for a safe and reliable means for measuring the quantity of a wasted injectable drug and testing the wasted injectable drug to verify the identity of the drug.

Methods for testing for the presence or absence of drugs are well known. One method of testing for the presence of a drug is to mix a reagent with the substance to be tested, which indicates the presence of a drug by a color change. Commonly known chemical reagents for color change indicia testing for the presence or absence of controlled substance drugs include Meyer's reagent, Marquis reagent, Nitric acid reagents, Cobalt Thiocyanate reagent, Dille-Koppany reagent, Mandeline reagent, Mecke's modified reagent, and Diazepam/Valium reagent. Classes of controlled substance drugs which are detectable through reagent color indicia testing include barbiturates, amphetamines, opiates, and synthetic opiates.

Another testing method employs an absorbent strip impregnated with a reagent which changes color if a particular substance is wicked into the absorbent strip. For example, when the absorbent strip is brought into contact with a narcotic solution, the strip, if designed to indicate the presence of the selected narcotic will change to a color which indicates the presence of that narcotic. A drug disposal and verification device is taught in U.S. Pat. No. 7,384,599 by Erdman and Brewer which is incorporated herein by reference as if repeated verbatim hereinafter.

BRIEF DESCRIPTION OF THE INVENTION

In order to overcome the above stated problems and limitations there is provided a drug disposal and verification device that is convenient and allows for the preservation of test results.

The drug disposal and verification device includes a housing which encloses a first chamber and a second chamber. The first chamber includes an injection port for receiving wasted fluid from a syringe and a sealed disposal volume which preferably contains an absorbent member for receiving and holding the wasted fluid. The positive displacement flow measuring device communicates between the injection port and the disposal volume. The drug disposal and verification device is arranged to receive wasted fluid through the injection port, measure the amount of fluid received while directing that fluid into the disposal volume and to divert a small fraction of the wasted fluid into the second chamber for chemical testing. Chemical testing may also occur in the disposal volume by means of at least one test strip. In the preferred embodiment, the positive displacement flow measuring device communicating between the injection port and the disposal volume is a hydraulic gear flow meter. The hydraulic gear flow meter includes intermeshing gears with gear teeth and tooth spaces between the teeth. The tooth spaces are sealed from on another by a close fit between the gears and the walls of the housing. The tooth spaces receive the wasted fluid from an inlet which communicates with the injection port and carries the wasted fluid to an outlet which communicates with the disposal volume. The amount of rotation of the gears of the hydraulic gear flow meter varies with the volume of wasted fluid flowing through the gear flow meter. Accordingly, the amount of gear rotation may be observed to measure the volume of fluid wasted. An absorbent test strip may also be housed in the first chamber for absorbing a small portion of the wasted fluid to provide a test result.

The tooth spaces between the teeth of the hydraulic gears have a standard tooth depth except for at least one special deep tooth space of substantially greater depth than other tooth spaces. During a portion of the cycle of rotation of the hydraulic gears, the at least one special deep tooth space exclusively communicates with a passageway leading into the second chamber. This allows the fluid carried in the at least one special deep tooth space to be transferred into the second chamber while the remaining fluid carried by the other standard depth tooth spaces is transferred to the disposal volume in the first chamber.

The second chamber of the housing contains at least one breakable ampule containing a testing reagent. The second chamber is arranged to allow the inflow of a small amount of wasted fluid and to enable a user to break the ampule containing the testing reagent after the small amount of wasted fluid has entered the second chamber. In the preferred embodiment, an ampule bracket is mechanically associated with a normally open valve in the passageway leading from the first chamber to the second chamber. The ampule bracket is arranged so that when the ampule is broken, the normally open valve closes and blocks the passageway leading from the first chamber to the second chamber. In this embodiment, the second chamber wall has a protrusion which is positioned adjacent to the ampule. External manual pressure applied to the protrusion from outside the second chamber will cause the protrusion to break the ampule. This releases the testing reagent within the ampule for testing the small portion of wasted fluid previously transferred into the second chamber.

DETAILED DESCRIPTION

Figure 1:
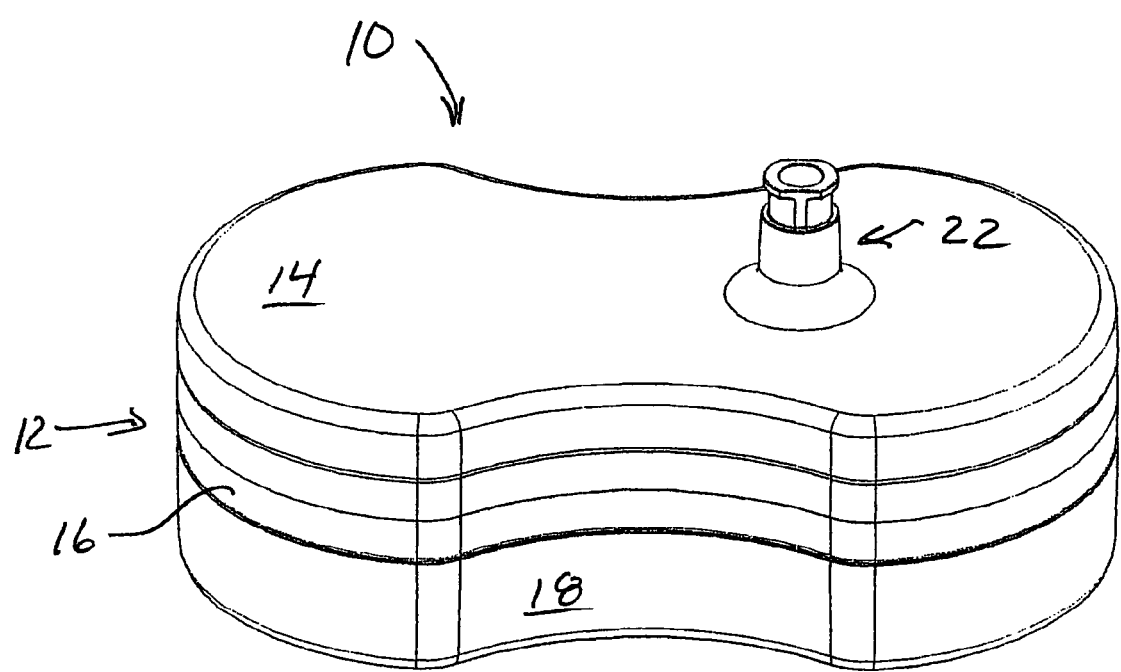
FIG. 1 is a perspective view of the drug assay and disposal device.
Figure 2:
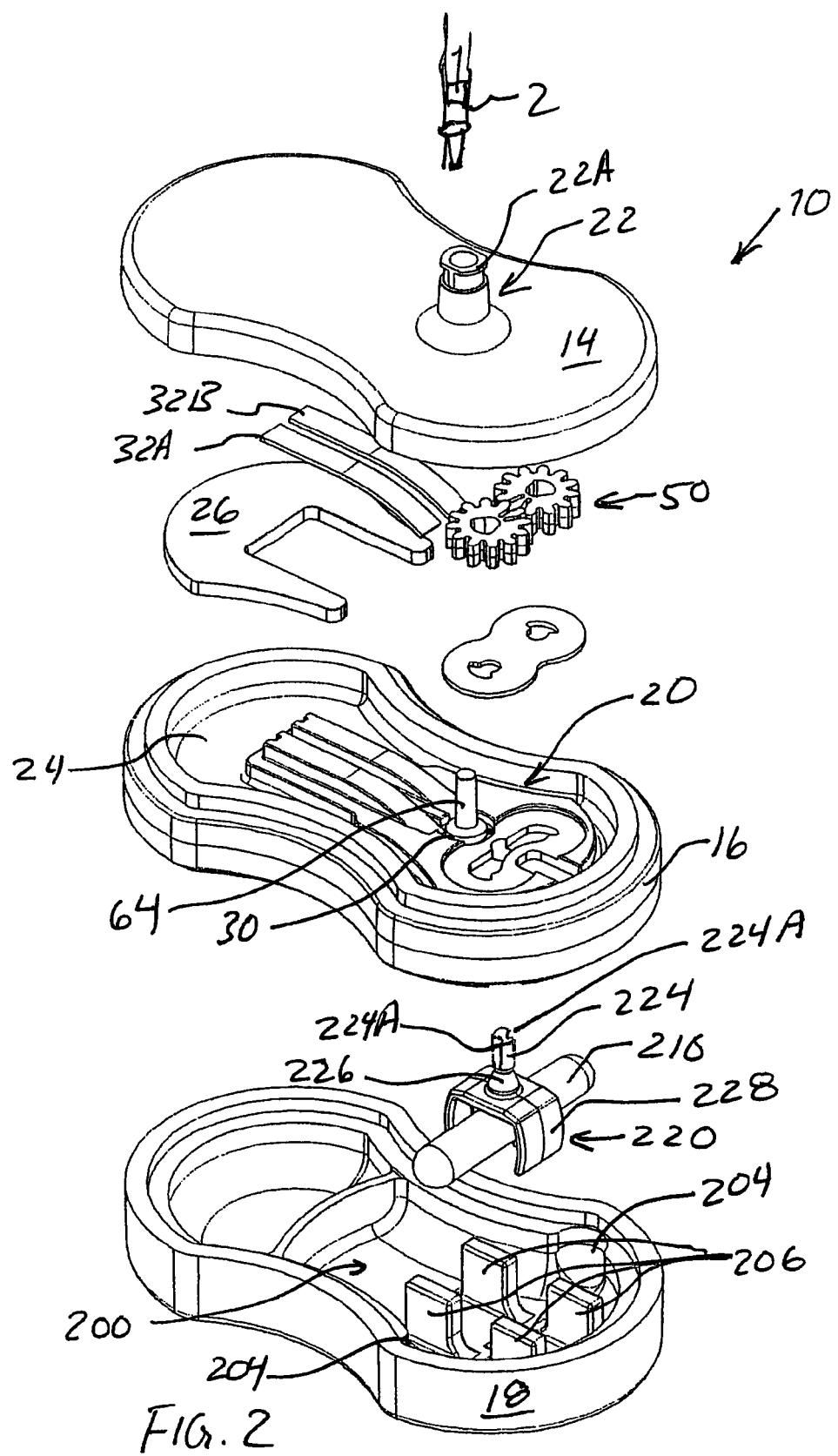
FIG. 2 is an exploded perspective view of the drug disposal and verification device.

Referring to the drawings, FIGS. 1 and 2 illustrate a preferred embodiment of a drug disposal and verification device 10. In general, drug disposal and verification device 10 may be fashioned to include a three part housing 12 which encloses a first chamber 20 and a second chamber 200. In this embodiment, housing 12 includes an upper portion 14, a center portion 16 and a lower portion 18.

As can be seen in FIG. 2, first chamber 20 is defined by upper portion 14 and center portion 16 of housing 12. First chamber 20 includes an injection port 22, a sealed disposal volume 24, an absorbent body 26 enclosed within disposal volume 24 and a hydraulic gear flow meter 50. Hydraulic gear flow meter 50 includes an inlet which is in communication with injection port 22 and an outlet in communication with disposal volume 24. A pair of chemical test strips 32A and 32B are sealed within first chamber 20 and communicate with the inlet of gear flow meter 50. An opening communicates between first chamber 20 and second chamber 200 for conveying a small portion of the wasted fluid from first chamber 20 to second chamber 200.

Second chamber 200 is defined by center portion 16 and lower portion 18 of housing 12. Second chamber 200 carries a breakable ampule 210 which contains a testing reagent for testing the small portion of wasted fluid conveyed into second chamber 200. Ampule 210 is also held by the spaced fingers of a clamp bracket 220. The design and operation of clamp bracket 220 will be described in detail below.

As noted above, first chamber 20 is defined by upper portion 14 and center portion 16 of housing 12. First chamber 20 is arranged to: (a) receive an injectable drug for wasting from a syringe, (b) measure the volume of injectable drug wasted, (c) perform at least one qualitative test on the injectable drug and (d) to transfer a relatively small fraction of the wasted injectable drug to second chamber 200 for further testing.

Figure 3A:
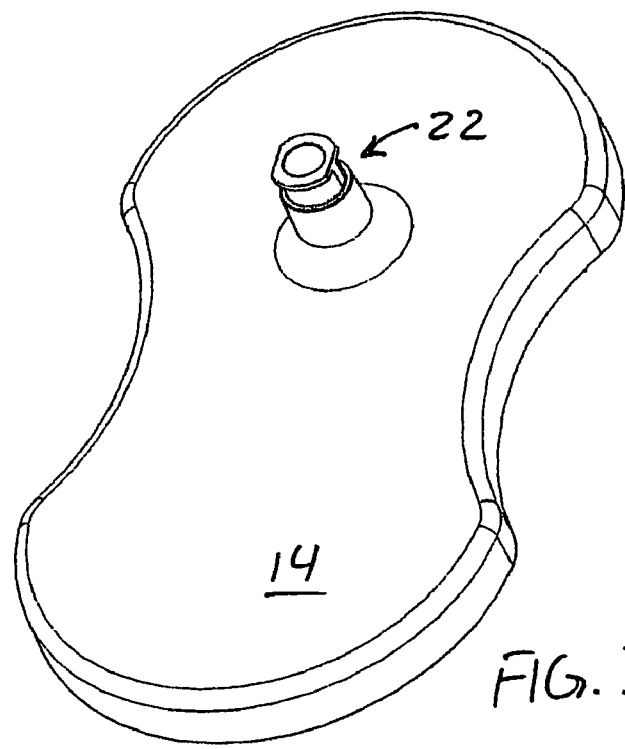
FIG. 3A is a perspective view showing the top side of the upper portion of the housing of the drug disposal and verification device.
Figure 3B:
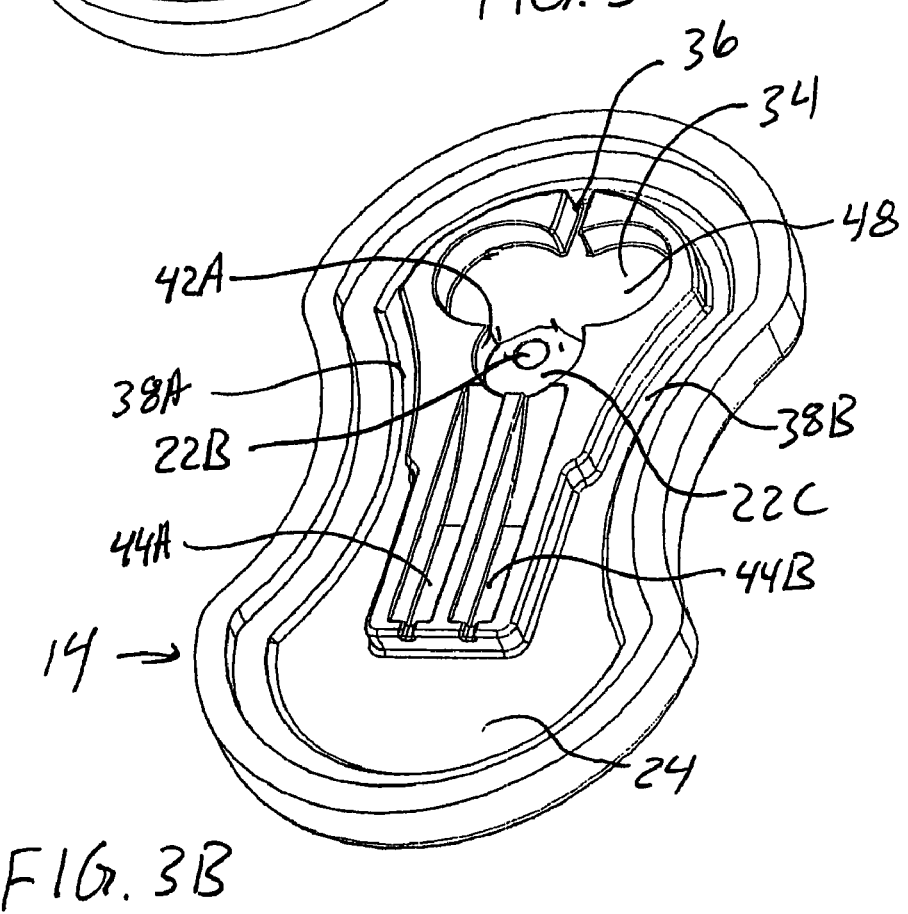
FIG. 3B is a perspective view showing the bottom side of the upper portion of the housing of the drug disposal and verification device.
Figure 4B:
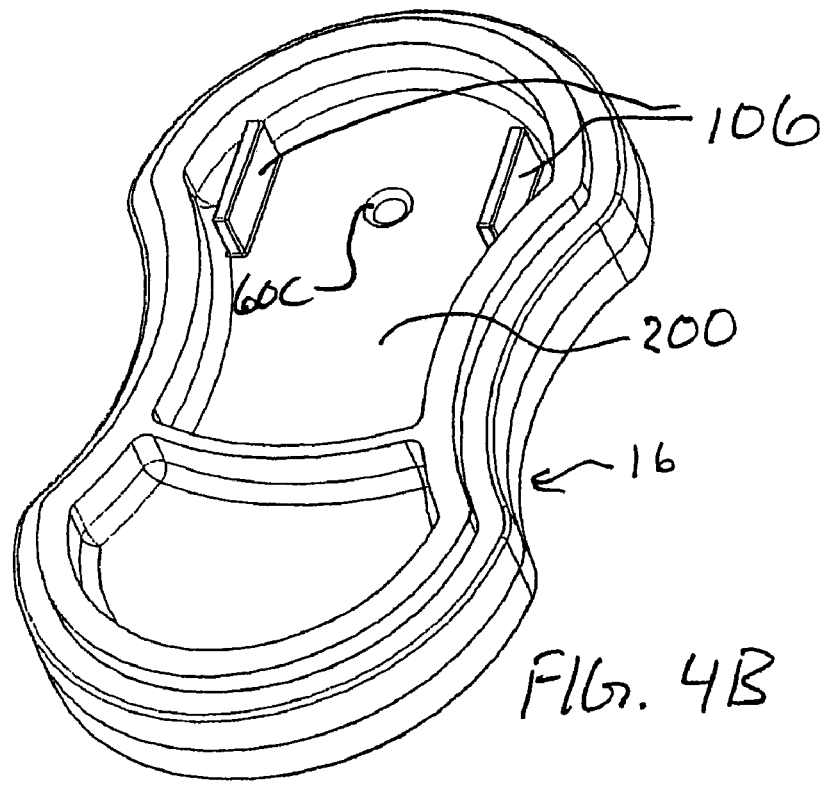
FIG. 4B is a perspective view showing the bottom side of the center portion of the housing of the drug disposal and verification device.
Figure 4A:
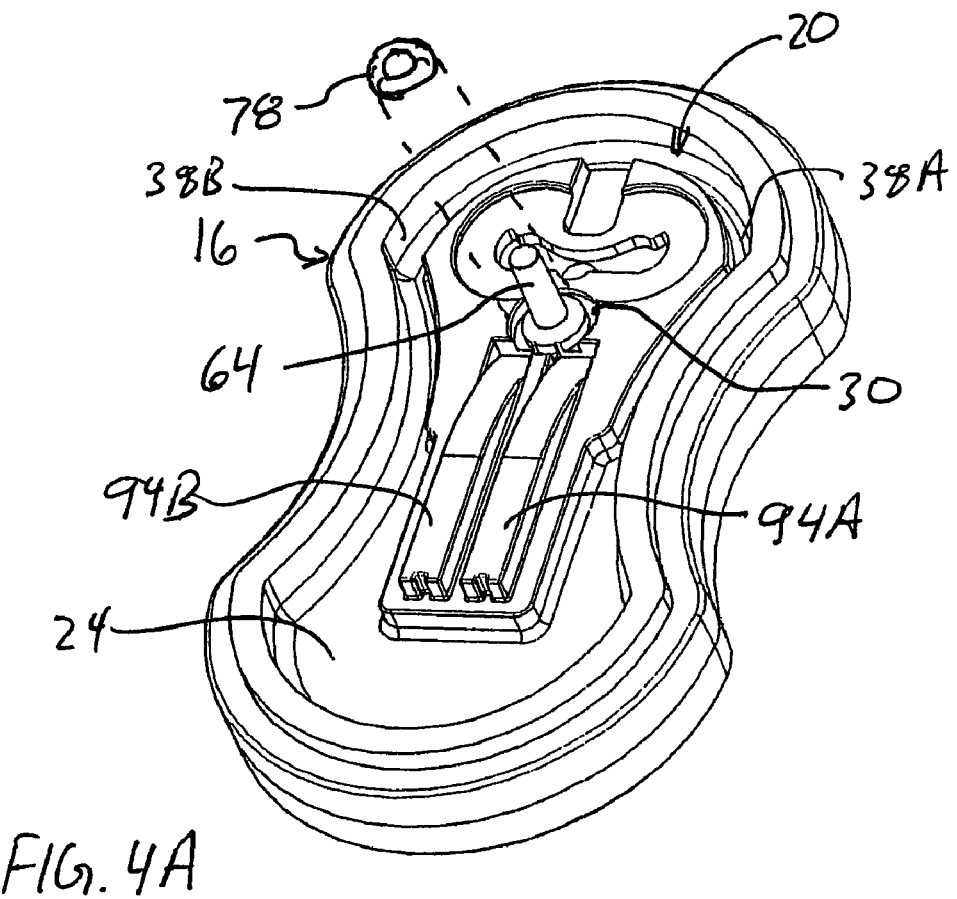
FIG. 4A is a perspective view showing the top side of the center portion of the housing of the drug disposal and verification device.
Figure 5B:
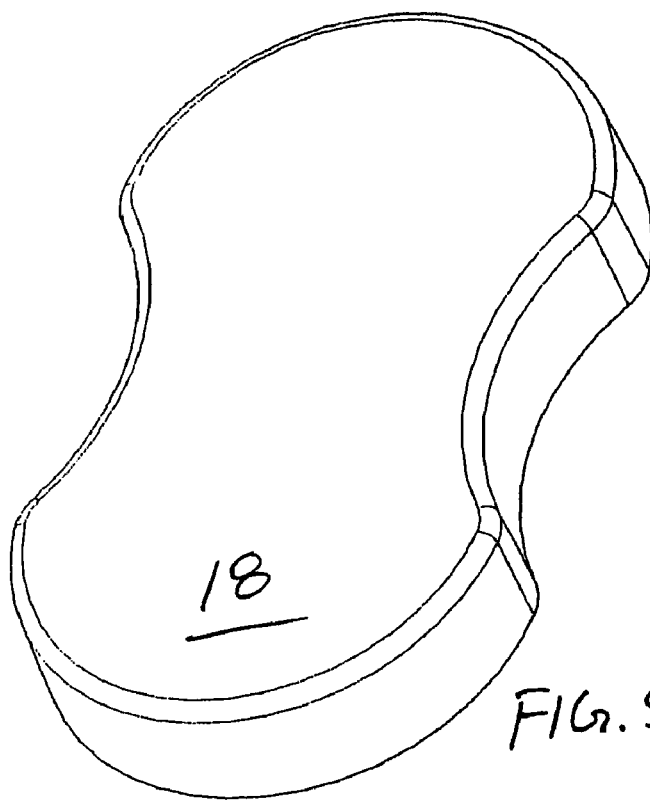
FIG. 5B is a perspective view showing the bottom side of the lower portion of the housing of the drug disposal and verification device.
Figure 5A:
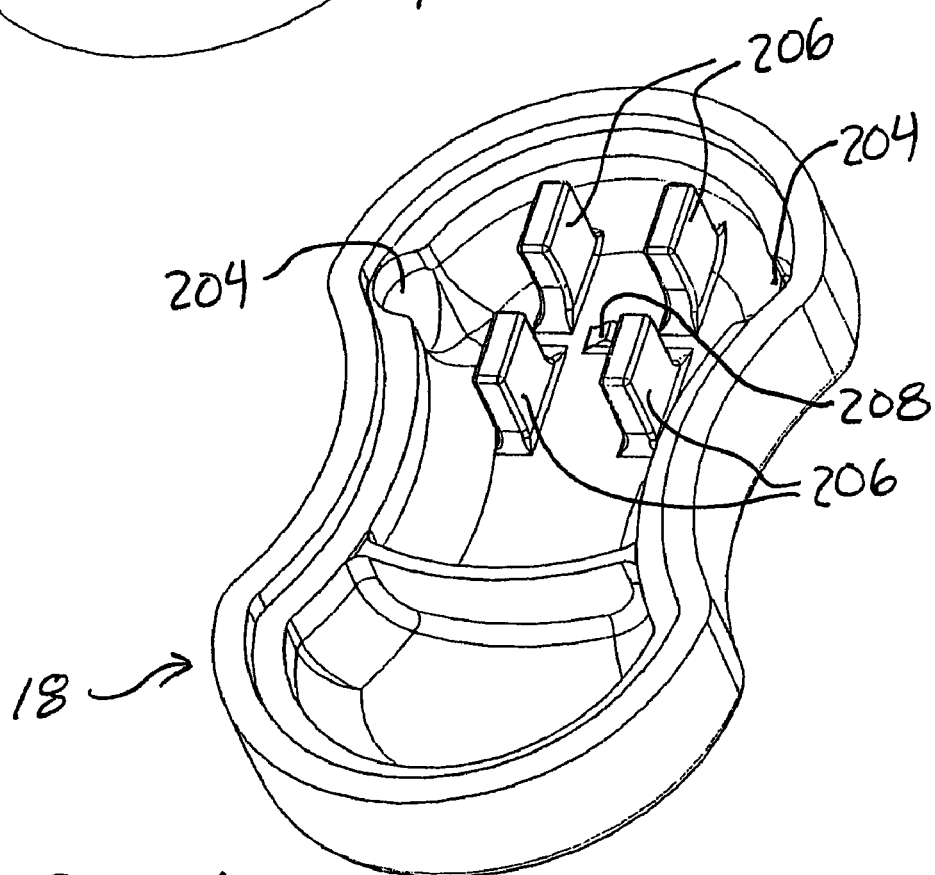
FIG. 5A is a perspective view showing the upper side of the lower portion of the housing of the drug disposal and verification device.

The interior surfaces of first chamber 20 can be best understood by referring to FIGS. 3B and 4A. FIG. 3B shows the lower surfaces of upper housing portion 14. FIG. 4A shows the corresponding upper surfaces of center housing portion 16. These corresponding surfaces define several features, namely, an injection port 22, a hydraulic gear flow meter inlet 30, two test strip channels 32A and 32B, a two part gear flow meter chamber 34, a gear flow meter outlet 36, waste flow channels 38A and 38B and disposal volume 24. Each of these features must be considered to understand the design and function of first chamber 20 and its included components.

Injection port 22 is shaped to receive and seal with the injection end of a syringe 2 which preferably has its injection needle removed. Injection port 22 includes a fitting 22A which seals with the injection end of syringe 2. Fitting 22A leads to a passageway 22B (shown in FIG. 3B) which preferably has a circular cross section. Passageway 22B terminates in a beveled surface 22C. Passageway 22B preferably increases in diameter towards its outlet to facilitate molding and removal from an injection mold. Beveled surface 22C slopes back toward the upper surface of upper housing portion 14. Center housing portion 16 has an elongated projection 64 which fits within passage 22B. The outer wall of elongated projection 64 and the inner wall of passageway 22B are slightly spaced from each other to define a narrow annular passage. Projection 64 is preferably tapered to match passageway 22B. This tapering of projection 64 also facilitates molding and mold release operations. Projection 64 terminates in a beveled base 66 which slopes in the opposite direction as beveled surface 22C. Beveled base 66 and beveled surface 22C are both contacted by a flexible torus shaped gasket 78 (shown in FIG. 4A) which seals off the annular passageway between passageway 22B and projection 64 from gear flow meter inlet 30. Gear flow meter inlet 30 leads to gear flow meter 50. The geometry of gear flow meter inlet 30 will be described in greater detail below. When under fluid pressure, gasket 78 expands and permits the flow of fluid from the annular passageway between passageway 22B and projection 64 to gear flow meter inlet 30. When no such pressure is available or when negative pressure is present, gasket 78 contracts and seals the annular passageway between passageway 22B and projection 64 from gear flow meter inlet 30. It is preferable, the annular passageway between passageway 22B and projection 64 be too narrow to allow passage of an injection needle and to control the flow rate of wasted fluid. This combined with the one way valve presented by gasket 78 prevents the withdrawal of a fluid from device 10 once the fluid has been injected.

Figure 2A:
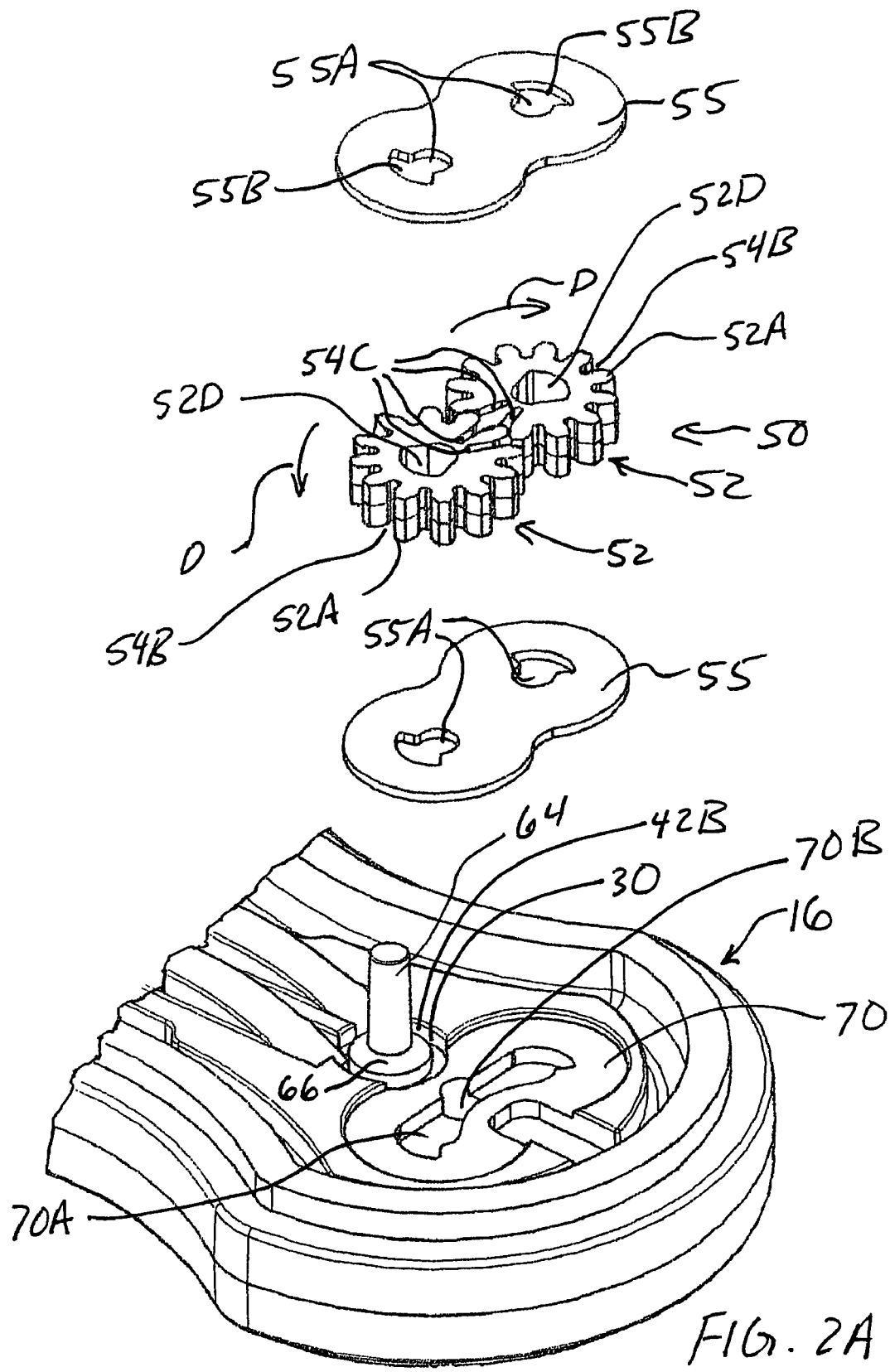
FIG. 2A is an exploded magnified perspective view of a portion of the drug disposal and verification device.

Gear flow meter inlet 30 receives wasted injectable drug from the annular passageway between passageway 22B and projection 64 as the injectable drug flows around gasket 78. The injectable drug flows through gear flow meter inlet 30 and into gear flow meter 50. The walls of gear flow meter inlet 30 are defined by surfaces of the under side of housing first portion 14 and surfaces of the top side of second housing portion 16. Beveled surface 22C surrounding inlet passageway 22B provides an upper wall for gear flow meter inlet 30. Gear flow meter inlet 30 is partially enclosed by a side wall 42A (shown in FIG. 3B) which extends downwardly from the perimeter of beveled surface 22C. Side wall 42A (shown in FIG. 3B) is continued by a second side wall 42B (shown in FIG. 2A) defined in second housing portion 16. Gear flow meter inlet 30 further includes an annular groove which surrounds beveled base 66 surrounding projection 64 as is shown in FIG. 2A. Gear flow meter inlet 30 preferably does not have a large capacity and is generally sufficient to provide a passageway for conveying fluid from injection port 22 to the intake of gear flow meter 50.

A pair of test strips 32A and 32B are enclosed between first housing portion 14 and second housing portion 16. Test strips 32A and 32B provide a primary and a secondary test for verifying the presence of a selected narcotic or controlled substance. These tests are qualitative in nature and may not be sensitive to concentration. Two tests are preferable because, those who wish to bypass a first test with a substitute solution will generally fail to bypass a second test with the same substitute solution. A positive indication from two tests verifies the presence of the selected narcotic or controlled substance. Test strips 32A and 32B are held between test strip recesses 44A and 44B in first housing portion 14 and test strip projections 94A and 94B of second housing portion 16. The tips of test strips 32A and 32B communicate with gear flow meter inlet 30 so that a small portion of the wasted fluid is wicked into test strips 32A and 32B. It is preferable to place test strips 32A and 32B in contact with gear flow meter inlet 30 because even a small amount of wasted injectable drug will interact with the test strips, even if there is not enough injectable drug to reach disposal volume 24.

Gear flow meter 50, which is best shown in FIG. 2A, is a positive displacement device for measuring the volume of flow between injection port 22 and disposal volume 24. Gear flow meter 50 performs two basic functions: First, gear flow meter 50 provides an indication of the amount of fluid wasted. Second, gear flow meter 50 diverts a small fraction of the wasted fluid to second chamber 200. Gear flow meter 50 is an example positive displacement flow measuring device selected for the preferred embodiment. Any one of a number of suitable positive displacement flow measuring devices having a feature for diverting a small fraction of the wasted fluid to the second chamber may be used to perform the functions of gear flow meter 50. Generally, gear flow meter 50 may preferably be a positive displacement liquid flow measuring gear set in which the amount of rotation in the gear set directly corresponds to an amount of liquid flow. In the preferred embodiment, gear flow meter 50 includes a first and second gears 52. Gears 52 are preferably involute gears. Hydraulic gear arrangements have long been used as hydraulic pumps, hydraulic turbines and hydraulic flow meters. The flow of fluid around gear flow meter 50 appears, at first glance, to be counter intuitive to the uninitiated. One might think that fluid would follow the shortest path and flow between gears 52 instead of around the perimeters of the turning gears. Meshed gear teeth between gears 52 present less surface area for responding to fluid pressure than the fully exposed surfaces of the unmeshed gear teeth to the right and the left of the incoming fluid. Accordingly, greater pressure is applied to the fully exposed gear teeth and thus the fluid flows around gears 52 causing right hand gear 52 to turn clockwise and left hand gear 52 to turn counter-clockwise as indicated by direction arrows D in FIG. 2A. The rate of flow into gear flow meter 50 is preferably limited by the small cross sectional area of the annular passageway between passageway 22B and projection 64. This prevents the gears of gear flow meter 50 from gaining enough angular momentum to continue spinning after fluid flow has ceased. Such an overspin would cause a false indication of the volume of fluid wasted. Gears 52 are preferably identical interfitting involute gears. The upper and lower surfaces of first and second gears 52 are bounded by a pair of generally identical thin gaskets 55 which each include identical, symmetrical openings 55A. The purpose of openings 55A will be described in greater detail below. Gears 52 and gaskets 55 are enclosed within gear recess 48 of upper housing portion 14 and a corresponding recess 70 of center housing portion 16. In this example, recess 70 of center portion 16 is sufficiently deep to receive one of gaskets 55, while recess 48 in upper housing portion 14 is sufficiently deep to receive the other of gaskets 55 and gears 52.

As can be understood by referring to FIG. 2A, gears 52 include corresponding interfitting preferably involute teeth 52A. Teeth 52A are separated by tooth spaces 54B which are generally of the same depth. However, each gear 52, in this example, includes two adjacent deep tooth spaces 54C which are significantly deeper than the other tooth spaces. The purpose of deep tooth spaces 54C is to receive a small quantity of wasted fluid and transfer it to second chamber 200. Deep tooth spaces 54C are located such that they are quickly encountered by fluid when fluid is injected into the unit. Gears 52 also include central fan shaped holes 52D.

As noted above, gears 52 are sandwiched between two gaskets 55. The openings 55A of gaskets 55 have enlarged fan shaped areas 55B. Fan shaped areas 55B are located generally opposite the initial positions of the deep tooth spaces 54C. When deep tooth spaces 54C rotate with gears 52 as fluid moves through gear flow meter 50, deep tooth spaces 54C align with fan shaped areas 55B. This alignment allows the small portion of fluid held in deep tooth spaces 54C to flow into a second recess 70A within gasket recess 70 of center portion 16. Second recess 70A in turn leads to a inter-chamber passage 70B which leads from first chamber 20 to second chamber 200. Openings 55A in gaskets 55 as well as the center openings 52D of gears 52 are arranged such that air from second chamber 200 may flow through the center openings 52D of gears 52, and through openings 55A of upper gasket 55 to replace the fluid in deep tooth spaces 54C thus preventing vapor lock.

The flow of the small portion of fluid from deep tooth spaces 54C to second chamber 200 as described above proceeds to inter-chamber passage 70B.

Figure 6A:
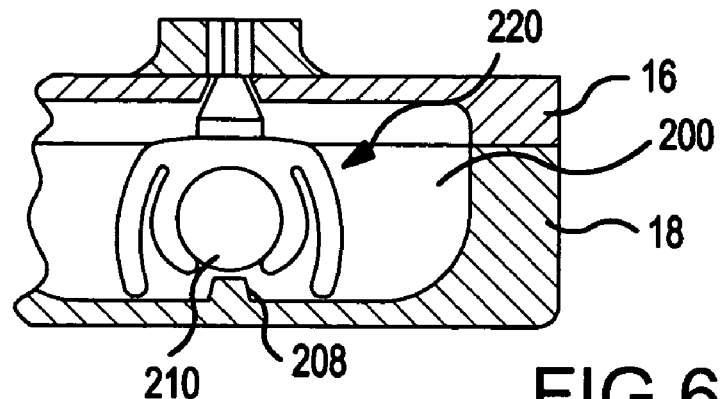
FIG. 6A is a first partial section view taken from plane A-A of FIG. 1 showing the ampule bracket in an open position spaced around an unfractured ampule of the drug disposal and verification device.
Figure 6B:
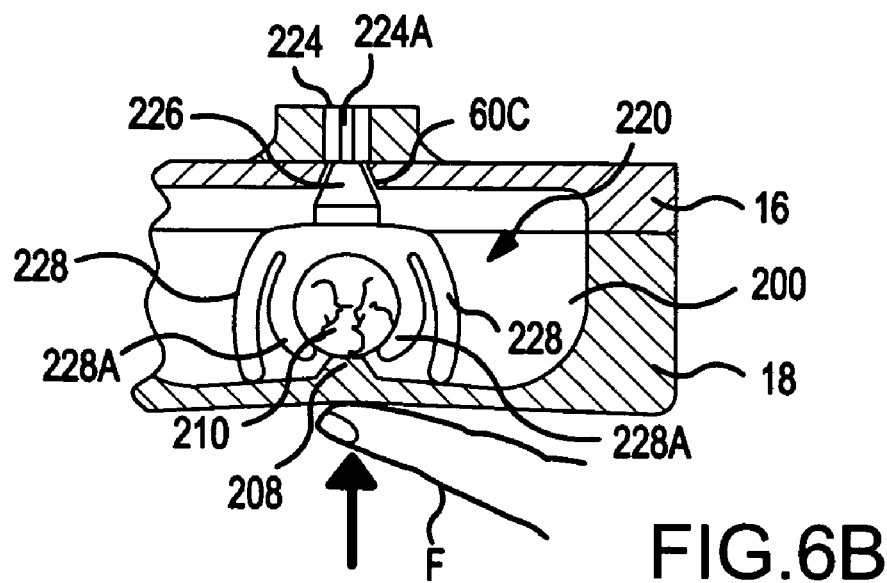
FIG. 6B is a second partial section view showing the ampule bracket in an open position spaced around an unfractured ampule and further showing a human appendage applying manual pressure causing translation of a second chamber wall projection and fracturing of the ampule.
Figure 6C:
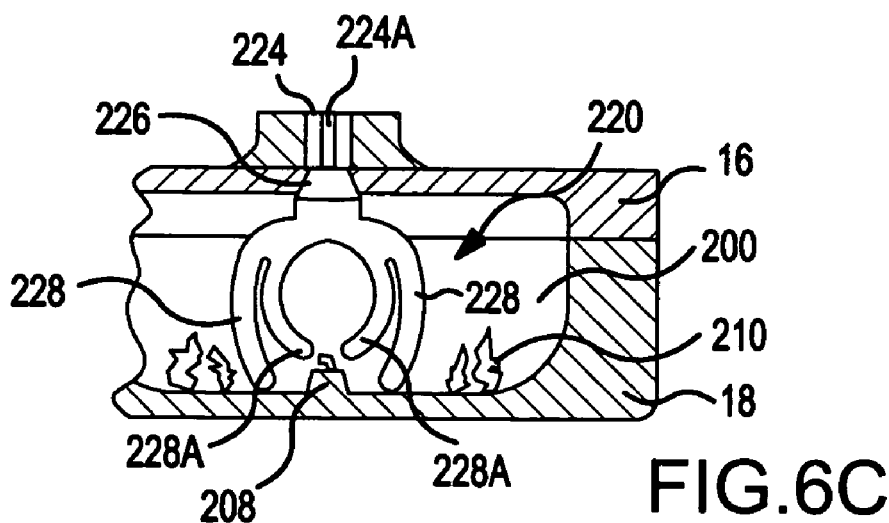
FIG. 6C is a third partial section showing the ampule bracket in a closed position after the ampule has fractured causing seating of the valve surface of the ampule bracket with the valve surface of the center portion of the housing.

Second chamber 200 houses a breakable ampule 210. Ampule 210 is retained by opposite recesses 204 and prongs 206 projecting from lower portion 18 as well as prongs 106 projecting from the lower surface of center portion 16 shown in FIG. 4B. Ampule 210 is also held by an ampule bracket 220. Ampule bracket 220 does not function to hold ampule 220 in place, rather ampule 210, when unbroken functions to maintain the position of ampule bracket 220. Ampule bracket 220 is part of a valve mechanism which closes communication between first chamber 20 and second chamber 200 when ampule 210 is broken. Ampule bracket 220 has a stem 224 which is received by inter-chamber passage 70B. Stem 224 includes opposite channels 224A for providing communication to first chamber 20 and the passage of the small portion of fluid from deep tooth spaces 54C. The lower portion of inter-chamber passage 70B opens into a cone shaped surface 60C shown in FIG. 4B. Ampule bracket 220 also includes a corresponding cone shaped surface 226 at the base of stem 212 for seating into and sealing with surface 60C. Ampule bracket 220, has two opposing fingers 228 extending below surface 226 which are biased toward a closed position shown in FIG. 6C. Opposing fingers 228 are mechanically associated with opposing inner fingers 228A which, in turn, are held apart by ampule 210 as shown in FIG. 6A as long as ampule 210 is unbroken. A tab 208 on the inside surface of the lower wall of lower portion 18 shown in FIGS. 6A-6C is deflected by external manual pressure by operator finger F as shown in FIG. 6B to cause ampule 210 to shatter thus releasing the test reagent contents of ampule 210. The shattering of ampule 210 also releases fingers 228A and 228 of ampule bracket 220 so that fingers 228 can move together. Fingers 228 and the floor of second chamber 200 are configured such that as fingers 228 move together they contact the floor of second chamber 200 and push ampule bracket 220 away from the floor of chamber 200 so that surface 226 of ampule bracket 220 seats with surface 60C at the base of inter-chamber passage 70B thus sealing off communication between first chamber 20 and second chamber 200. If the device has been operated correctly, a small amount of wasted injectable drug should be present in second chamber 200 when ampule 210 is shattered. The resulting limited reaction of only a small amount of injectable drug may be witnessed to verify the presence of a pre-selected drug. The limited scope of the reaction prevents an accumulation of heat and energy sufficient to cause any danger to an operator.

It is to be understood that while certain forms of this invention have been illustrated and described, it is not limited thereto, except in so far as such limitations are included in the following claims and allowable equivalents thereof.

Having thus described the invention, what is claimed as new and desired to be secured by Letters Patent is:

1. A drug disposal and verification device comprising:
a first chamber including an injection port for receiving wasted injectable drug from a syringe and a disposal volume for receiving and holding the wasted injectable drug,
a second chamber containing a breakable ampule that contains a testing reagent, the breakable ampule being breakable by external manual pressure,
a passageway communicating between the first chamber and the second chamber and a valve associated with the passageway that is normally open, the valve operable such that the valve closes the passageway when the ampule is broken,
a flow measuring device interposed between the injection port and the disposal volume of the first chamber, the flow measuring device further operable to divert a small portion of the wasted injectable drug into the passageway that communicates with the second chamber,
whereby when the wasted injectable drug is injected through the injection port, the positive displacement flow measuring device measures the volume of drug injected as most of the wasted injectable drug flows into the disposal volume and as a small portion of the wasted injectable drug is diverted to the second chamber wherein the small portion of wasted injectable drug is tested as the breakable ampule is broken by manual external pressure and as the valve closes the passageway between the first chamber and the second chamber.

2. The drug disposal and verification device of claim 1, wherein:
the disposal volume includes at least one test strip for indicating the presence of a drug.

3. The drug disposal and verification device of claim 1, wherein:
the normally open valve associated with the passageway communicating between the first chamber and the second chamber includes a bracket that holds the breakable ampule, and wherein the bracket and the normally open valve are operable such that when the ampule is broken the valve blocks the passageway between the first chamber and the second chamber.

4. A drug disposal and verification device comprising:
a first chamber including an injection port for receiving wasted injectable drug from a syringe and a disposal volume for receiving and holding the wasted injectable drug,
a second chamber holding a breakable ampule containing a drug test reagent and having at least one flexible wall, the ampule breakable by the application of manual external pressure to the at least one flexible wall,
the first chamber and the second chamber separated by a common wall having a inter-chamber passageway leading from the first chamber to the second chamber,
a positive displacement flow measuring device interposed between the injection port and the disposal volume of the first chamber for measuring the volume of wasted injectable drug flowing from the injection port to the disposal volume, the positive displacement flow measuring device also having a portion for diverting a small fraction of the wasted injectable drug to the second chamber,
a normally open valve in the passageway leading from the first chamber to the second chamber, an ampule bracket connected to the normally open valve for holding the ampule, the ampule bracket and the valve operable such that breakage of the ampule causes movement of the bracket and closing of the valve thereby blocking the passageway leading from the first chamber to the second chamber,
whereby a volume of a wasted injectable drug may be injected into the injection port causing the positive displacement flow measuring device to indicate the volume of the wasted injectable drug flowing into the disposal volume and diversion of a small portion of the wasted injectable drug through the inter-chamber passageway into the second chamber for subsequent testing with the reagent of the ampule when the ampule is broken by external manual pressure, the breaking of the ampule also causing the valve connected to the ampule bracket to block the inter-chamber passageway.

5. The drug disposal and verification device of claim 4, wherein:
the ampule bracket moves between an open position and a closed position, and the passageway communicating between the first chamber and the second chamber and the ampule bracket have corresponding cone shaped surfaces that seal the passageway when the ampule bracket is in the closed position.

6. A drug disposal and verification device comprising,
a first chamber including an injection port adapted for receiving wasted injectable drug from a syringe, the first chamber including a disposal volume for receiving and holding the wasted injectable drug,
a second chamber holding a breakable ampule containing a drug test reagent, the second chamber having at least one flexible wall, the ampule disposed within the chamber so that the ampule may be broken by the application of manual external pressure to the at least one flexible wall,
the first chamber and the second chamber separated by a common wall having a inter-chamber passageway leading from the first chamber to the second chamber,
a hydraulic gear flow meter interposed between the injection port of the first chamber and the disposal volume of the first chamber, the hydraulic gear flow meter having at least one hydraulic gear for generally measuring the volume of wasted injectable drug flowing from the injection port into the disposal volume, the at least one hydraulic gear including a plurality of gear teeth disposed around the perimeter thereof wherein adjacent gear teeth define inter-tooth spaces for receiving and conveying wasted injectable drug, at least two adjacent gear teeth defining at least one deep tooth space having a radial depth greater than the other tooth spaces, the at least one deep tooth space for capturing a small portion of the wasted fluid during a portion of the rotation of the at least one gear, the at least one deep tooth space exclusively communicating with the inter-chamber passageway, an ampule bracket mechanically associated with the ampule and a normally open valve that is associated with the inter-chamber passageway, the ampule bracket and the valve arranged such that breakage of the ampule causes movement of the bracket and closing of the valve thereby closing communication between the second chamber and the first chamber, whereby a volume of wasted injectable drug may be injected into the injection port causing rotation of the gear flow meter for indicating the volume of wasted injectable drug flowing into the disposal volume and diversion of a small portion of wasted injectable drug from the at least one deep tooth space through the inter-chamber passageway into the second chamber for subsequent testing with the reagent of the ampule when the ampule is broken by external manual pressure, the breaking of the ampule also causing the valve connected to the ampule bracket to close the inter-chamber passageway.

7. The drug disposal and verification device of claim 6, wherein:

the ampule bracket moves between an open position and a closed position, and the passageway leading from the first chamber to the second chamber and the ampule bracket have corresponding cone shaped surfaces that close the passageway when the ampule bracket is in the closed position.

8. The drug disposal and verification device of claim 6, wherein:

the ampule bracket moves between an open position and a closed position, and the ampule bracket includes opposing fingers which clasp the breakable ampule and which move together when the breakable ampule is broken and push against an inside wall of the second chamber so that the ampule bracket moves from the open position to the closed position when the ampule is broken, whereby the passageway between the first and second chambers is closed when the ampule is broken.

9. The drug disposal and verification device of claim 6, wherein:

the ampule bracket moves between an open position and a closed position, the passageway leading from the first chamber to the second chamber and the ampule bracket have corresponding cone shaped surfaces that seal the passageway when the ampule bracket is in the closed position, the ampule bracket also includes opposing fingers which that clasp the breakable ampule, the opposing fingers of the ampule bracket arranged such that when the ampule is broken, the opposing fingers move together and push against an inside wall of the second chamber such that the ampule bracket moves from the open position to the closed position, whereby, when the ampule is broken, the passageway between the first and second chambers is plugged when the ampule is broken.

* * * * *